US00PP25242P2

(12) United States Plant Patent
Miyazaki

(10) Patent No.: US PP25,242 P2
(45) Date of Patent: Jan. 20, 2015

(54) ***LOBELIA* PLANT NAMED 'SUNLOBECOSUBU'**

(50) Latin Name: *Lobelia erinus*
Varietal Denomination: Sunlobecosubu

(71) Applicant: Kiyoshi Miyazaki, Shiga (JP)

(72) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 175 days.

(21) Appl. No.: 13/694,492

(22) Filed: Dec. 6, 2012

(51) Int. Cl.
*A01H 5/00* (2006.01)

(52) U.S. Cl.
USPC ..... Plt./451

(58) Field of Classification Search
CPC ..... A01H 5/02
USPC ..... Plt./451
See application file for complete search history.

*Primary Examiner* — June Hwu
(74) *Attorney, Agent, or Firm* — C. A. Whealy

(57) ABSTRACT

A new and distinct cultivar of *Lobelia* plant named 'Sunlobecosubu', characterized by its compact, semi-upright and mounding plant habit; vigorous growth habit; freely branching habit; dense and bushy plant form; freely flowering habit; long flowering period; and light violet blue-colored flowers.

1 Drawing Sheet

Botanical designation: *Lobelia erinus*.
Cultivar denomination: 'SUNLOBECOSUBU'.

BACKGROUND OF THE INVENTION

The present invention relates to a new and distinct cultivar of *Lobelia* plant, botanically known as *Lobelia erinus* and hereinafter referred to by the name 'Sunlobecosubu'.

The new *Lobelia* plant is a product of a planned breeding program conducted by the Inventor in Higashiomi, Shiga, Japan. The objective of the breeding program is to create new *Lobelia* plants freely branching and bushy plant habit and attractive flower coloration.

The new *Lobelia* plant originated from a cross-pollination made by the Inventor in April, 2006 of a proprietary selection of *Lobelia erinus* identified as code number 6Lob-HL1, not patented, as the female, or seed, parent with a proprietary selection of *Lobelia erinus* identified as code number 6Lob-ab, not patented, as the male, or pollen, parent. The new *Lobelia* plant was discovered and selected by the Inventor as a single flowering plant with the progeny of the stated cross-pollination in a controlled greenhouse environment in Higashiomi, Shiga, Japan in May, 2007.

Asexual reproduction of the *Lobelia* plant by vegetative cuttings in Higashiomi, Shiga, Japan since May, 2007 has shown that the unique features of this new *Lobelia* plant are stable and reproduced true to type in successive generations.

SUMMARY OF THE INVENTION

Plants of the new *Lobelia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunlobecosubu'. These characteristics in combination distinguish 'Sunlobecosubu' as a new and distinct *Lobelia* plant:

1. Compact, semi-upright and mounding plant habit.
2. Vigorous growth habit.

3. Freely branching habit; dense and bushy plant form.
4. Freely flowering habit.
5. Long flowering period.
6. Light violet blue-colored flowers.

Plants of the new *Lobelia* differ primarily from plants of the female parent selection in the following characteristics:

1. Plants of the new *Lobelia* are shorter than plants of the female parent selection.
2. Plants of the new *Lobelia* and the female parent selection differ in flower color as plants of the female parent selection have white-colored flowers.

Plants of the new *Lobelia* differ primarily from plants of the male parent selection in flower color as plants of the male parent selection have darker violet blue-colored flowers.

Plants of the new *Lobelia* can be compared to plants of *Lobelia erinus* 'Loboudtis', disclosed in U.S. Plant Pat. No. 15,526. In side-by-side comparisons conducted in Higashiomi, Shiga, Japan, plants of the new *Lobelia* differed from plants of 'Loboudtis' in the following characteristics:

1. Plants of the new *Lobelia* were taller and bushier than and not as outwardly spreading than plants of 'Loboudtis'.
2. Leaves of plants of the new *Lobelia* were narrowly elliptic in shape whereas leaves of plants of 'Loboudtis' were broadly ovate in shape.
3. Upper petals of plants of the new *Lobelia* were broader than upper petals of plants of 'Loboudtis'.
4. Plants of the new *Lobelia* and 'Loboudtis' differed in flower color as plants of 'Loboudtis' had darker violet blue-colored flowers.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the top of the sheet comprises a side perspective view of a typical flowering plant of 'Sunlobecosubu' grown in a container.

The photograph at the bottom of the sheet is a close-up view of a typical flowering plant of 'Sunlobecosubu'.

DETAILED BOTANICAL DESCRIPTION

Plants used for the aforementioned photographs and following description were grown during the summer in 15-cm containers in an outdoor nursery in Higashiomi, Shiga, Japan and under cultural practices typical of commercial *Lobelia* production. During the production of the plants, day temperatures averaged 23° C. and night temperatures averaged 13° C. Plants were four months old when the photographs and the description were taken. In the following description, color references are made to The Royal Horticultural Society Colour Chart, 2001 Edition, except where general terms of ordinary dictionary significance are used.

Botanical classification: *Lobelia erinus* 'Sunlobecosubu'.

Parentage:

*Female, or seed, parent*.—Proprietary selection of *Lobelia erinus* identified as code number 6Lob-HL1, not patented.

*Male, or pollen, parent*.—Proprietary selection of *Lobelia erinus* identified as code number 6Lob-ab, not patented.

Propagation:

*Type cutting*.—Vegetative cuttings.

*Time to initiate roots, summer and winter*.—About one week at 15° C. to 20° C.

*Time to produce a rooted young plant, summer and winter*.—About three weeks at 15° C. to 20° C.

*Root description*.—Fine, fibrous; white in color.

*Rooting habit*.—Freely branching.

Plant description:

*Plant and growth habit*.—Compact, semi-upright and mounding plant habit; freely branching habit with lateral branches developing at potentially every node; relatively short internodes; dense and bushy plant habit; vigorous growth habit.

*Plant height*.—About 44.5 cm.

*Plant width*.—About 25 cm.

*Lateral branch description*.—Diameter: About 1.4 mm. Internode length: About 1.7 cm. Strength: Strong, flexible. Aspect: Upright to outwardly. Texture: Pubescent. Color: Close to 137A.

Foliage description:

*Arrangement*.—Alternate, simple; sessile.

*Length*.—About 3.2 cm.

*Width*.—About 8 mm.

*Shape*.—Narrowly elliptic.

*Apex*.—Acute.

*Base*.—Obtuse.

*Margin*.—Crenate.

*Texture, upper and lower surfaces*.—Slightly pubescent.

*Venation pattern*.—Pinnate.

*Color*.—Developing leaves, upper surface: Close to 137A. Developing leaves, lower surface: Close to 137C. Fully expanded leaves, upper surface: Close to 137B; venation, close to 137D. Fully expanded leaves, lower surface: Close to 138B; venation, close to 137D.

Flower description:

*Flower arrangement, habit and shape*.—Flowers typically arranged in terminal and lateral racemes; flowers held mostly outwardly; freely flowering habit with typically two to six flowers per inflorescence and about 265 flowers per plant; flowers bilabiate with two upper petals and three larger lower petals.

*Fragrance*.—None detected.

*Natural flowering season*.—In Japan, plants of the new *Lobelia* flower from May until October; plants begin flowering about three to four weeks after planting.

*Flower longevity on the plant*.—Longevity of individual flowers is highly dependent on temperature, flowers typically last about 10 to 14 days on the plant; flowers persistent.

*Flower length*.—About 1.4 cm.

*Flower diameter*.—About 1.4 cm.

*Flower tube length*.—About 9.7 mm.

*Flower tube diameter*.—About 3.2 mm.

*Flower buds*.—Length: About 12.9 mm. Diameter: About 3.9 mm. Shape: Club-shaped. Color: Close to 150C.

*Petals*.—Arrangement: Single whorl of five petals fused towards the base; two upper petals and three larger lower petals. Upper petals: Length, beyond throat: About 5.4 mm. Width: About 2.6 mm. Shape: Elliptic. Apex: Acute. Margin: Entire. Texture, upper and lower surfaces: Smooth, glabrous. Lower petals: Length, beyond throat: About 7.8 mm. Width: About 5.1 mm. Shape: Ovate. Apex: Rounded. Margin: Entire. Texture, upper and lower surfaces: Smooth, glabrous. Color, upper petals: When opening, upper surface: Close to 96D. When opening, lower surface: Close to 97B. Fully opened, upper surface: Close to 97A. Fully opened, lower surface: Close to 97C. Color, lower petals: When opening, upper surface: Close to 96D; towards the base, close to NN155C. When opening, lower surface: Close to 97B. Fully opened, upper surface: Close to 97A; towards the base, close to NN155C. Fully opened, lower surface: Close to 97C. Color, throat: Close to NN155C; spots, close to 94B; nectar guides, close to 154A. Color, tube: Close to 97D.

*Sepals*.—Arrangement: Single whorl of five sepals, fused at the base; star-shaped calyx. Length: About 6.2 mm. Width: About 1.3 mm. Shape: Narrowly deltoid. Apex: Acute. Margin: Entire. Texture, upper and lower surfaces: Slightly pubescent. Color, upper and lower surfaces: Close to 143B, occasionally tinged with red-purple.

*Pedicels*.—Length: About 2.2 cm. Diameter: About 0.4 mm. Strength: Strong, flexible. Texture: Pubescent. Color: Close to 144A.

*Reproductive organs*.—Stamens: Quantity per flower: Five. Stamen length: About 7 mm. Anther length: About 2 mm. Anther width: About 1 mm. Anther shape: Oblong, fused. Anther color: Close to 93B. Pollen amount: Scarce. Pollen color: Close to NN155B. Pistils: Quantity per flower: One. Pistil length: About 8.8 mm. Stigma shape: Bi-lobate. Stigma color: Close to 86C. Style color: Close to 145B. Ovary color: Close to 145A.

*Fruits and seeds*.—Fruit and seed development have not been observed on plants of the new *Lobelia*.

Disease & pest resistance: Plants of the new *Lobelia* have not been noted to be resistant to pathogens and pests common to *Lobelia* plants.

Garden performance: Plants of the new *Lobelia* have been observed to have good garden performance and to tolerate wind, rain and temperatures ranging from about 5° C. to about 28° C.

It is claimed:

1. A new and distinct *Lobelia* plant named 'Sunlobeco-subu' as illustrated and described.

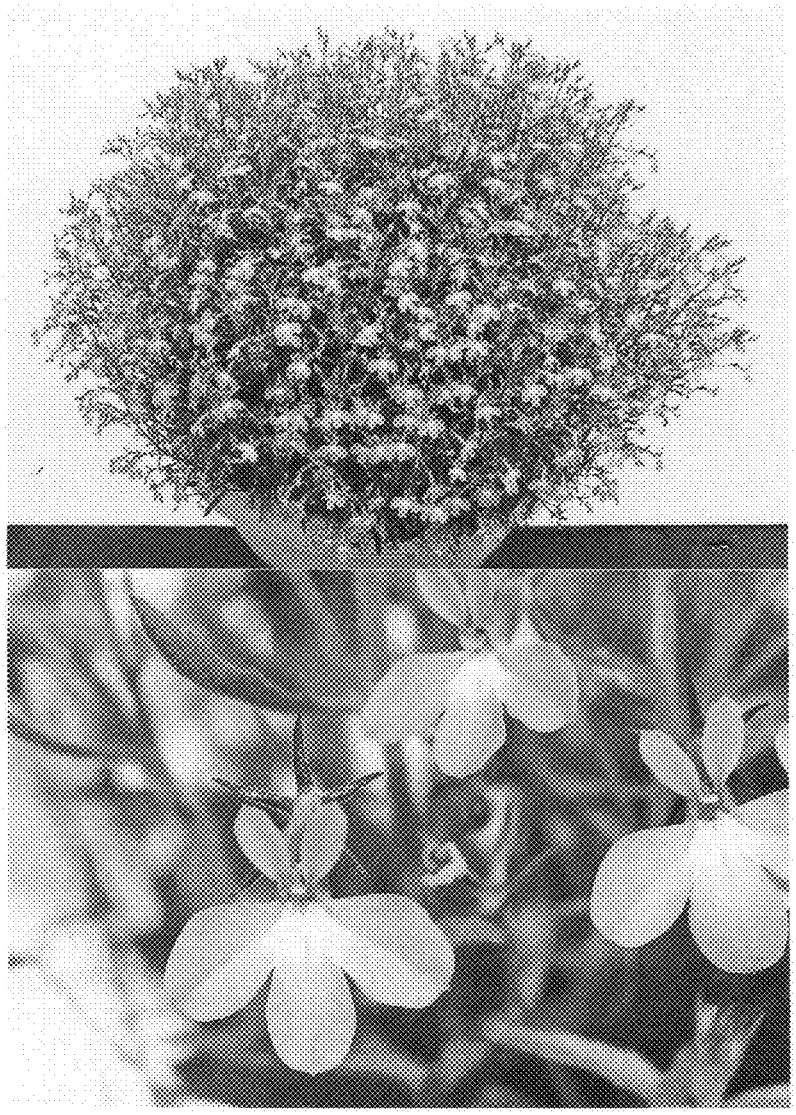

* * * * *